United States Patent [19]
Giolito et al.

[11] 4,103,096
[45] Jul. 25, 1978

[54] PREPARATION OF META-ALKYLPHENOLS

[75] Inventors: Silvio L. Giolito, Whitestone, N.Y.;
Stanley B. Mirviss, Stamford, Conn.

[73] Assignee: Stauffer Chemical Company,
Westport, Conn.

[21] Appl. No.: 841,626

[22] Filed: Oct. 13, 1977

[51] Int. Cl.² .............................................. C07C 39/06
[52] U.S. Cl. .................................................... 568/783
[58] Field of Search ........... 260/621 E, 624 E, 624 R,
260/624 C, 621 D

[56] References Cited
U.S. PATENT DOCUMENTS

| 3,839,470 | 10/1974 | Biler | 260/624 E |
| 3,878,255 | 4/1975 | Norell | 260/624 R |
| 3,932,537 | 1/1976 | Wetzel et al. | 260/624 C |

Primary Examiner—James O. Thomas, Jr.
Assistant Examiner—Werren B. Lone
Attorney, Agent, or Firm—William C. Gerstenzang

[57] ABSTRACT

Meta-alkylphenols are prepared by the isomerization of nonmeta-alkylphenols in the presence of trifluoromethane sulfonic acid. Ortho-isomer-containing alkylphenols are isomerized to increase their meta-isomer content and reduce their ortho-isomer content.

9 Claims, No Drawings

PREPARATION OF META-ALKYLPHENOLS

BACKGROUND OF THE INVENTION

The present invention relates to the preparation of meta-alkylphenols. More particularly, the present invention relates to the preparation of meta-alkylphenols by the isomerization of nonmeta-alkylphenols.

The most common method for preparing alkylphenols comprises the alkylation of phenol with an olefin in the presence of a Friedel-Crafts catalyst. The product of this alkylation reaction generally comprises a mixture of several isomeric forms of the alkylphenol. These mixtures often contain little or no meta-isomer. For many purposes, however, the meta-isomers are more desirable than either the ortho- or para-isomers.

It is, therefore, desirable to be able to isomerize non-meta-alkylphenols to the meta-isomer.

Several methods have been proposed for preparing meta-alkylphenols by isomerization of other alkylphenol isomers. Thus, for example, in Japanese patent publication 45-30091/1970, it is disclosed that an alkylphenol may be isomerized in the liquid phase by heating in the presence of a two-component catalyst consisting of one part by weight of silica-alumina-type catalyst and an amount of aluminum-phenoxide catalyst corresponding to no more than 0.6 part by weight of aluminum metal. After removal of unreacted phenol, the remaining alkylphenol fraction is said to contain over 70% meta-alkylphenol. The use of a nonsoluble solid catalyst in the reaction mixture, however, presents a number of difficulties. For example, the solid catalyst is more difficult to handle than a liquid catalyst would be, and the final removal of the catalyst upon completion of the reaction represents an additional process step in and of itself.

U.S. Pat. No. 3,014,079 discloses that meta-alkylated hydroxy aromatic compounds may be prepared by heating an ortho-or para-alkylated hydroxy aromatic compound, such as tertiary-butylphenol or isopropylphenol, with a corresponding hydroxy aromatic compound, such as phenol, in the presence of a strong acid and clay. The requirement that both a clay and a hydroxy aromatic compound be present in the reaction mixture imposes serious limitations on this method.

It has been shown (J. Org. Chem., 38, 1929 (1973)) that meta-tertiary-butylphenol may be prepared by alkylating phenol with isobutylene in solvent quantities of HF to form a product which is principally meta-tertiary-butylphenol and 3,5-ditertiary-butylphenol. The handling difficulties associated with HF, however, detract somewhat from the luster of this method as a commercial process.

Therefore, a need exists for a method for forming meta-alkylphenols which requires neither the handling of difficult-to-handle materials such as HF nor special process steps for the removal of solid catalyst.

It is, therefore, a primary object of this invention to provide a new method for preparing meta-alkylphenols from nonmeta-alkylphenols which requires neither the handling of difficult-to-handle materials nor the employment of special process steps to remove solid catalyst from the final product.

It is a further object of this invention to provide a method for preparing a meta-alkylphenol from phenol and an olefin.

It is yet another object of this invention to provide a method for increasing the meta-isomer content and reducing the ortho-isomer content of an ortho-isomer-containing alkylphenol.

Surprisingly and unexpectedly, we have discovered that meta-alkylphenols may be formed by the isomerization of nonmeta-alkylphenols in the presence of trifluoromethane sulfonic acid. This method for forming meta-alkylphenols is highly efficient and requires neither the handling of difficult-to-handle materials nor the employment of special process steps to remove solid catalyst.

In accordance with one aspect of this invention, there is provided a method for preparing a meta-alkylphenol from a nonmeta-alkylphenol which comprises contacting the nonmeta-alkylphenol with trifluoromethane sulfonic acid at a concentration ranging from about 0.01 to about 5% by weight of alkylphenol at a temperature ranging from about 120° C. to about the reflux temperature of the alkylphenol for a period of time sufficient to convert at least a portion of the nonmeta-alkylphenol to meta-alkylphenol.

The meta-alkylphenols which may be prepared in accordance with the method of this invention include, but are not limited to, those having alkyl groups which contain from 2 to about 12 carbon atoms. Meta-alkylphenols which may be prepared in accordance with the method of this invention to particular advantage, and which are preferred, are meta-isopropylphenol and meta-butylphenol. There are, of course, several isomeric forms of the alkyl portion of the meta-butylphenols which may be prepared in accordance with this invention. These include the sec-butyl and tertiary-butyl forms. A particularly preferred meta-alkylphenol which may be prepared in accordance with the method of this invention is meta-tertiary-butylphenol.

The nonmeta-alkylphenols from which meta-alkylphenols may be prepared in accordance with the method of this invention include, but are not limited to, those having alkyl groups which contain from 2 to about 12 carbon atoms. Nonmeta-alkylphenols which are preferably converted to meta-alkylphenols in accordance with the method of this invention comprise nonmeta-alkylphenols selected from the group consisting of ortho-isopropylphenol, para-isopropylphenol, mixtures of ortho- and para-isopropylphenol, ortho-tertiary-butylphenol, para-tertiary-butylphenol, and mixtures of ortho- and para-tertiary-butylphenol.

The reaction by which the nonmeta-alkylphenols are isomerized to meta-alkylphenols may be conducted under vacuo, at atmospheric or at elevated pressures. The temperature at which the reaction is conducted varies from about 120° C. to about the reflux temperature of the reaction mixture. The reflux temperature will, of course, vary in accordance with the pressure at which the reaction is being conducted.

While the method of this invention is most advantageously employed to prepare meta-alkylphenols from other alkylphenol isomers, it is also advantageously employed to prepare a meta-alkylphenol from an olefin and phenol. In preparing a meta-alkylphenol from an olefin and phenol in the practice of this invention, the alkylation of phenol with an olefin to form an alkylphenol and the isomerization of the alkylphenol formed to increase its meta-isomer content are accomplished in a single process. Thus, in accordance with another aspect of this invention, there is provided a method for preparing a meta-alkylphenol which comprises forming a mixture of an olefin and phenol at an olefin/phenol molar ratio ranging from about 0.2/1 to about 2/1, reacting the mixture at a temperature ranging from about 120° C. to about the reflux temperature of the mixture in the presence of trifluoromethane sulfonic acid at a concentration ranging from about 0.01 to about 5% by weight of mixture to form an alkylphenol reaction mixture containing nonmeta-alkylphenol, and maintaining the alkylphenol reaction mixture at a temperature ranging from about 120° C. to about the reflux temperature of the alkylphenol reaction mixture for a period of time sufficient to convert at least a portion of the nonmeta-alkylphenol to meta-alkylphenol.

The meta-alkylphenols which may be prepared in accordance with this embodiment of the invention include, but are not limited to, those meta-alkylphenols having alkyl groups which contain from 2–12 carbon atoms. Particularly preferred meta-alkylphenols which may be prepared in accordance with this embodiment are meta-isopropylphenol and meta-tertiary-butylphenol.

The olefins which are mixed with phenol and reacted in accordance with this embodiment include, but are not limited to, those olefins having from 2 to 12 carbon atoms. Particularly preferred olefins are propylene and isobutylene.

In accordance with yet another aspect of this invention, there is provided a method for increasing the meta-alkylphenol content and reducing the ortho-alkylphenol content of an ortho-alkylphenol-containing alkylphenol which comprises contacting the ortho-alkylphenol with trifluoromethane sulfonic acid at a concentration ranging from about 0.01 to about 5% by weight of alkylphenol at a temperature ranging from about 120° C. to about the reflux temperature of the alkylphenol for a period of time sufficient to convert at least a portion of the ortho-alkylphenol to meta-alkylphenol.

In a particularly useful embodiment, the ortho-alkylphenol-containing alkylphenol is contacted with the trifluoromethane sulfonic acid for a period of time sufficient to convert at least a portion of the ortho-alkylphenol to meta-alkylphenol and reduce the ortho-alkylphenol content of the alkylphenol to less than 1% by weight. It will, of course, be understood that the decrease in ortho-alkylphenol content does not necessarily match the increase in meta-alkylphenol content since isomers other than meta may be formed, and isomers other than ortho, if present, may be isomerized to the meta-isomer. The net result, however, is an increase in meta-isomer content and a reduction in ortho-isomer content.

The ortho-alkylphenol which is brought into contact with trifluoromethane sulfonic acid in the practice of this invention may be one component of a mixture of alkylphenols, or it may be a pure component. Where the ortho-alkylphenol is a part of a mixture, the entire mixture may be brought into contact with the trifluoromethane sulfonic acid, or the ortho-alkylphenol may be separated from the mixture and independently brought into contact with the trifluoromethane sulfonic acid.

As is the case in all aspects of this invention, the reaction by which the ortho-alkylphenol is converted to meta-alkylphenol may be conducted under vacuo, atmospheric, or elevated pressure. As in the other embodiments, the reflux temperature of the reaction mixture will vary in accordance with the pressure at which the reaction is being conducted.

The ortho-alkylphenols which are isomerized in accordance with this embodiment of the invention include, but are not limited to those ortho-alkylphenols having alkyl groups which contain from 2–12 carbon atoms. Particularly preferred are ortho-isopropylphenol and ortho-tertiary-butylphenol although ortho-tertiary-butylphenol is most preferred.

The objects of this invention are made possible by the surprising and unexpected discovery that trifluoromethane sulfonic acid, a catalyst which is soluble in phenol as well as in many alkylphenols, is effective in promoting the isomerization of ortho- and/or para-alkylphenols to their meta-isomers at relatively low concentrations of trifluoromethane sulfonic acid. Thus, for example, we have been able to isomerize a major portion of the ortho- and para-tertiary-butylphenols contained in a tertiary-butylphenol mixture to the meta-isomer using a trifluoromethane sulfonic acid concentration of only 0.5% by weight.

The alkylphenols which are isomerized to form meta-alkylphenols in accordance with the practice of this invention may in themselves be prepared by any of a number of methods known in the art. In perhaps the best known method, an alkylphenol is prepared by alkylating phenol with an olefin in the presence of an appropriate catalyst at a temperature ranging from about 100° to about 250° C. Appropriate catalysts for this purpose include Friedel-Crafts catalysts such as aluminum chloride, boron trifluoride, and the like; acid catalyst such as sulfonic acid, para-toluenesulfonic acid, and the like; and acidic clays such as montmorillonite clay, and the like.

The product of the alkylation reaction will, in most cases, consist of mixture of several alkylphenol isomers. For example, when phenol is alkylated with isobutylene, the product can include ortho-tertiary-butylphenol, para-tertiary-butylphenol, meta-tertiary-butylphenol, 2,4-ditertiary-butylphenol, 2,4,6-tri-tertiary-butylphenol, and the like. The amount of meta-isomer present in these mixtures, however, is often so low as to be "non detectable" by ordinary chromatographic analysis techniques.

The meta-alkylphenol content of these mixtures may be easily and effectively increased through the practice of the present invention.

In accordance with this invention, the alkylphenol isomer or mixture of isomers which is to be isomerized is brought into contact with trifluoromethane sulfonic acid at a temperature and for a period of time sufficient to promote the isomerization of nonmeta-alkylphenol isomers to meta-alkylphenol isomers.

Contact of the alkylphenol with trifluoromethane sulfonic acid may be accomplished by any of those techniques known in the art for contacting chemical reactants with catalysts. Since trifluoromethane sulfonic acid is readily soluble in phenol and many alkylphenols, a preferred technique is to add the trifluoromethane sulfonic acid directly to the reaction mixture in liquid form. The trifluoromethane sulfonic acid may be added "neat" or as a solution in phenol, the alkylphenol being isomerized, or other appropriate solvent. Since the total amount of trifluoromethane sulfonic acid required is generally quite small, it will be found most convenient to add it to the reaction mixture as a dilute solution in which form the amount added may be accurately metered or measured.

When used in the form of a liquid which is miscible with the other components of the reaction mixture, the trifluoromethane sulfonic acid may be easily added or continuously metered to the reaction mixture. When used in this form, the trifluoromethane sulfonic acid may also be readily removed from the product upon completion of the reaction. Thus, for example, upon completion of the reaction, the trifluoromethane sulfonic acid may be left unneutralized or neutralized with any convenient base. Then, when the reaction mass is subsequently purified by distillation, the neutralized or unneutralized trifluoromethane sulfonic acid remains in the distillation bottoms, which may then be discarded. Since the crude reaction mass does not have to be washed to remove spent catalyst, there are no large amounts of waste water to be disposed of.

The trifluoromethane sulfonic acid may also be added to the reaction mixture in the form of a heterogeneous catalyst such as that formed by impregnating a clay or other particulate substrate with the trifluoromethane sulfonic acid or adsorbing the trifluoromethane sulfonic acid onto a clay or other particulate substrate. The advantages offered by this type of catalyst such as, for example, the ability to recover and recycle the catalyst, often outweigh the inconveniences associated with the preparation and use of heterogneous catalysts.

The concentration of trifluoromethane sulfonic acid used will vary in accordance with many factors such as the design of the reactor being used, the temperature and pressure at which the reaction is being conducted, the mode of the reaction (batch or continuous), the reaction rate desired, the presence of a solvent, and other such factors, all of which are easily determined by those skilled in the art. We have found that trifluoromethane sulfonic acid concentrations ranging from about 0.01% to about 5% by weight of alkylphenol are effective under most circumstances although concentrations ranging from about 0.025 to about 2.0% are preferred.

The time period required to effect the isomerization of nonmeta-alkylphenol isomers to meta-alkylphenol will vary in accordance with a number of factors such as, for example, the degree of isomerization desired. Additional factors, which also effect the time required, are the concentration of trifluoromethane sulfonic acid in the reaction mixture and the temperature at which the reaction is being conducted. Satisfactory results may generally be achieved in time periods ranging from about 1 to about 36 hours although, where it is desired to approach equilibrium conditions, time periods of up to 50 hours or more may be required.

Although the reaction may be conducted over a relatively wide temperature range such as from about 120° C. to about the reflux temperature of the reaction mixture (about 185°–190° C. at atmospheric pressure), we prefer to conduct the isomerization reaction at reflux temperature. The reflux temperature may, of course, vary in accordance with the pressure at which the reaction is being conducted. The pressure, in turn, may vary from vacuo to several atmospheres depending on the needs of the individual practitioner.

The invention will be further illustrated in the following nonlimiting examples.

EXAMPLE 1

A mixture of tertiary-butylphenol isomers (500 grams) was added to a 250-ml. round-bottom flask together with 1.0 gram (0.5 weight percent) trifluoromethane sulfonic acid. The charge was heated to reflux temperature (185° C.) while stirring and maintained at this temperature for 18 hours.

Samples of the original tertiary-butylphenol mixture and the final product after 18 hours at reflux were each analyzed by gas chromatography with the following results:

| Component | Original Mixture (Weight Percent) | Final Product (Weight Percent) |
|---|---|---|
| Phenol | 44.1 | 50.9 |
| Ortho-tertiary-butylphenol | 7.7 | 0.4 |
| Meta-tertiary-butylphenol | — | 35.0 |
| Para-tertiary-butylphenol | 44.9 | 9.3 |
| 2,6-ditertiary-butylphenol | 0.1 | 0.2 |
| 2,4-ditertiary-butylphenol | 3.1 | 2.7 |
| 2,5- + 3,5-tertiary-butylphenol | — | 0.1 |
| Tritertiary-butylphenol | — | 0.4 |
| Others | 0.1 | 1.0 |

EXAMPLE 2

A mixture of isopropylphenol isomers (100 grams) was added to a 250-ml. round-bottom flask together with 2.0 grams (2% by weight) trifluoromethane sulfonic acid. The charge was heated to reflux temperature (185°–190° C.) and maintained at this temperature for 18 hours.

Samples of the original isopropylphenol mixture and the final product after 18 hours at reflux were analyzed by gas chromatography with the following results:

| Component | Original Mixture (Weight Percent) | Final Product (Weight Percent) |
|---|---|---|
| Phenol | 47.1 | 37.8 |
| Unknown | — | 0.6 |
| Ortho-isopropylphenol | 28.6 | 7.4 |
| Meta-isopropylphenol | 0.0 | 16.4 |
| Para-isopropylphenol | 7.2 | 15.1 |
| Unknown | — | 0.3 |
| 2,6-diisopropylphenol | 6.9 | 0.3 |
| 2,4-diisopropylphenol | 6.3 | 3.6 |
| 2,5- + 3,5-di-isopropylphenol | 1.2 | 4.4 |
| Others | 2.7 | 14.1 |

EXAMPLE 3

Para-tertiary-butylphenol in the amount of 100 grams was added to a 250-ml. round-bottom flask together with 1.0 gram (1% by weight) trifluoromethane sulfonic acid. The charge was then heated while stirring to reflux temperature (185°–190° C.) and maintained at this temperature for 18 hours. The resulting product was analyzed by gas chromatography with the following results:

| Component | Percent by Weight in Product |
|---|---|
| Phenol | 31.5 |
| Unknown | 2.3 |
| Ortho-tertiary-butylphenol | 0.7 |
| Meta-tertiary-butylphenol | 24.8 |
| Para-tertiary-butlyphenol | 11.4 |
| Unknown | 4.3 |
| 2,6-ditertiary-butylphenol | 0.5 |
| Unknown | 2.0 |
| 2,4-ditertiary-butylphenol | 0.8 |
| 2,5- + 3,5-ditertiary-butylphenol | 6.8 |

| Component | Percent by Weight in Product |
|---|---|
| 2,4,6-tritertiary butylphenol | 2.1 |
| Others | 12.8 |

While these illustrative examples demonstrate the practice of this invention in conjunction with a batch-type process using a mixture of alkylphenol isomers, it will be understood that the method of the invention may also be practiced in a continuous process and may be applied to single isomeric components as well as to mixtures.

As used herein, the term "alkylphenol" when not designated as a specific isomer, such as ortho- or para-, is defined as meaning either a single isomer or an isomeric mixture such as those which result from the Friedel-Crafts alkylation of phenol. As mentioned earlier, such mixtures may contain unreacted phenols, mono-isomers such as meta-, para- and ortho- as well as diisomers such as 2,6-; 2,4-; etc.

It can be seen from the preceding examples that the method of this invention enables the effective and efficient preparation of meta-alkylphenols from other alkylphenol isomers. It is also seen that meta-alkylphenols may be prepared from an olefin and phenol by a single process in accordance with the method of this invention. As has been shown, the method of this invention is effective and efficient and requires neither the handling of difficult-to-handle materials such as HF nor the employment of special process steps to remove solid catalyst.

It will thus be seen that the objects set forth above are effectively attained and, since certain changes may be made in the above-method without departing from the scope of the invention, it is intended that all matter contained in the above-description shall be interpreted as illustrative and not in a limiting sense.

What is claimed is:

1. A method for preparing a meta-monoalkylphenol from a nonmeta-monoalkylphenol wherein said meta-monoalkylphenol is a meta-monoalkylphenol having an alkyl group which contains from about 2 to about 12 carbon atoms which comprises contacting said nonmeta-monoalkylphenol with trifluoromethane sulfonic acid at a concentration ranging from about 0.01 to about 5% by weight of alkylphenol at a temperature ranging from about 120° C to about the reflux temperature of said meta-monoalkylphenol for a period of time sufficient to convert at least a portion of said nonmeta-monoalkylphenol to meta-monoalkylphenol.

2. The method for preparing a meta-monoalkylphenol from a nonmeta-monoalkylphenol in accordance with claim 1 wherein said meta-monoalkylphenol is meta-isopropylphenol or meta-tertiary-butylphenol and said nonmeta-monoalkylphenol is ortho-isopropylphenol, para-isopropylphenol, a mixture of ortho- and para-isopropylphenol, ortho-tertiary-butylphenol, para-tertiary-butylphenol or a mixture of ortho- and para-tertiary-butylphenol.

3. The method for preparing a meta-monoalkylphenol from a nonmeta-monoalkylphenol in accordance with claim 2 wherein said temperature is a temperature ranging from about 120° to about 190° C.

4. The method for preparing a meta-monoalkylphenol from a nonmeta-monoalkylphenol in accordance with claim 4 wherein said period of time is a period of time ranging from about 1 to about 36 hours.

5. The method for preparing a meta-monoalkylphenol from a nonmeta-monoalkylphenol in accordance with claim 4 wherein said method is conducted at atmospheric pressure.

6. A method for increasing the meta-monoalkylphenol content and reducing the ortho-isomer content of an ortho-monoalkylphenol-containing alkylphenol wherein said alkylphenol is an alkylphenol having alkyl groups which contain from about 2 to about 12 carbon atoms which comprises contacting said ortho-monoalkylphenol with trifluoromethane sulfonic acid at a concentration ranging from about 0.01% to about 5% by weight of alkylphenol at a temperature ranging from about 120° C to about the reflux temperature of said alkylphenol for a time sufficient to convert at least a portion of said ortho-monoalkylphenol to meta-monoalkylphenol.

7. The method of increasing the meta-monoalkylphenol content and reducing the ortho-monoalkylphenol content of an ortho-monoalkyl-containing alkylphenol in accordance with claim 6 wherein said meta-monoalkylphenol is meta-isopropylphenol or meta-tertiary-butylphenol and said ortho-monoalkylphenol is ortho-isopropylphenol or ortho-tertiary-butylphenol.

8. The method of increasing the meta-monoalkylphenol content and reducing the ortho-monoalkylphenol content of an ortho-monoalkylphenol-containing alkylphenol in accordance with claim 7 wherein said temperature ranges from about 120° to about 190° C, and said period of time ranges from about 1 hour to about 36 hours.

9. The method of increasing the meta-monoalkylphenol content and reducing the ortho-monoalkylphenol content of an ortho-monoalkylphenol-containing alkylphenol in accordance with claim 8 wherein said method is conducted at atmospheric pressure.

* * * * *